(12) United States Patent
Jones et al.

(10) Patent No.: US 6,554,849 B1
(45) Date of Patent: Apr. 29, 2003

(54) INTRAVASCULAR EMBOLIZATION DEVICE

(75) Inventors: Donald K. Jones, Lauderhill, FL (US); Vladimir Mitelberg, Aventura, FL (US)

(73) Assignee: Cordis Corporation, Miami Lakes, FL (US)

( * ) Notice: Subject to any disclaimer, the term of this patent is extended or adjusted under 35 U.S.C. 154(b) by 400 days.

(21) Appl. No.: 09/659,475

(22) Filed: Sep. 11, 2000

(51) Int. Cl.⁷ .............................................. A61M 29/00
(52) U.S. Cl. ..................................................... 606/200
(58) Field of Search ................. 606/151, 113, 606/114, 157, 158, 200, 198; 623/1.1, 1.11, 1.12, 1.15, 1.16, 1.18, 1.19, 1.2, 1.22

(56) References Cited

U.S. PATENT DOCUMENTS

| | | |
|---|---|---|
| 4,512,338 A | 4/1985 | Balko et al. |
| 4,577,631 A | 3/1986 | Kreamer |
| 4,662,885 A | 5/1987 | DiPisa, Jr. |
| 4,710,192 A | 12/1987 | Liotta et al. |
| 4,994,069 A | 2/1991 | Ritchart et al. |
| 4,994,071 A | 2/1991 | MacGregor |
| 5,108,407 A | 4/1992 | Geremia et al. |
| 5,122,136 A | 6/1992 | Guglielmi et al. |
| 5,258,020 A | 11/1993 | Froix |
| 5,527,338 A * | 6/1996 | Purdy .......................... 606/200 |
| 5,551,954 A | 9/1996 | Buscemi et al. |
| 5,772,668 A | 6/1998 | Summers et al. |
| 5,773,668 A | 6/1998 | Fertel et al. |
| 5,776,219 A | 7/1998 | Jinbo et al. |
| 5,925,063 A | 7/1999 | Khosravi |
| 5,928,260 A | 7/1999 | Chin et al. |
| 6,113,622 A | 9/2000 | Hieshima |
| 6,254,612 B1 * | 7/2001 | Hieshima ..................... 606/108 |

* cited by examiner

Primary Examiner—David O. Reip
Assistant Examiner—D Jacob Davis
(74) Attorney, Agent, or Firm—Henry W. Collins

(57) ABSTRACT

An intravascular embolization device and deployment system in which the embolization device may be collapsed and placed within a catheter for delivery by the deployment system to a preselected site within a vessel. After placement the embolization device returns to its initial preformed configuration within the vessel.

22 Claims, 2 Drawing Sheets

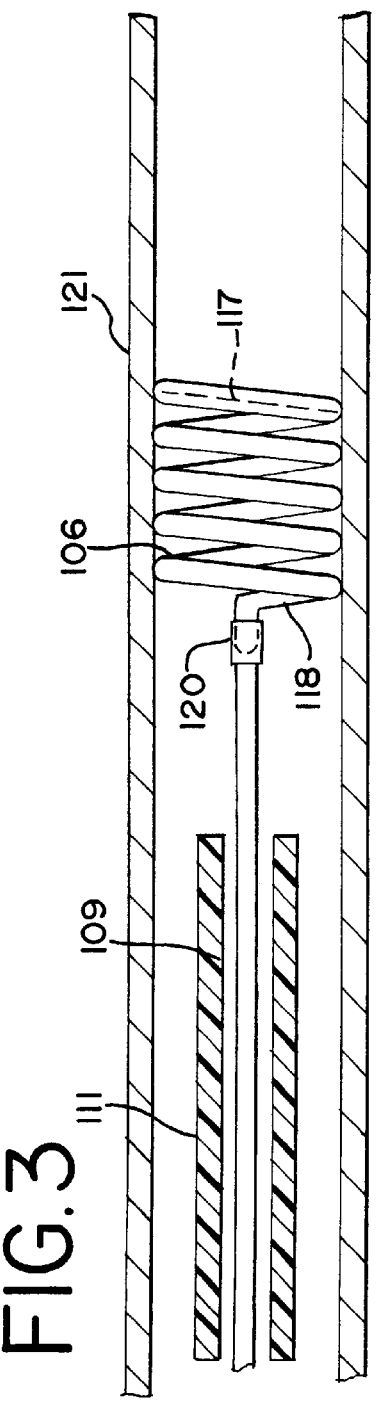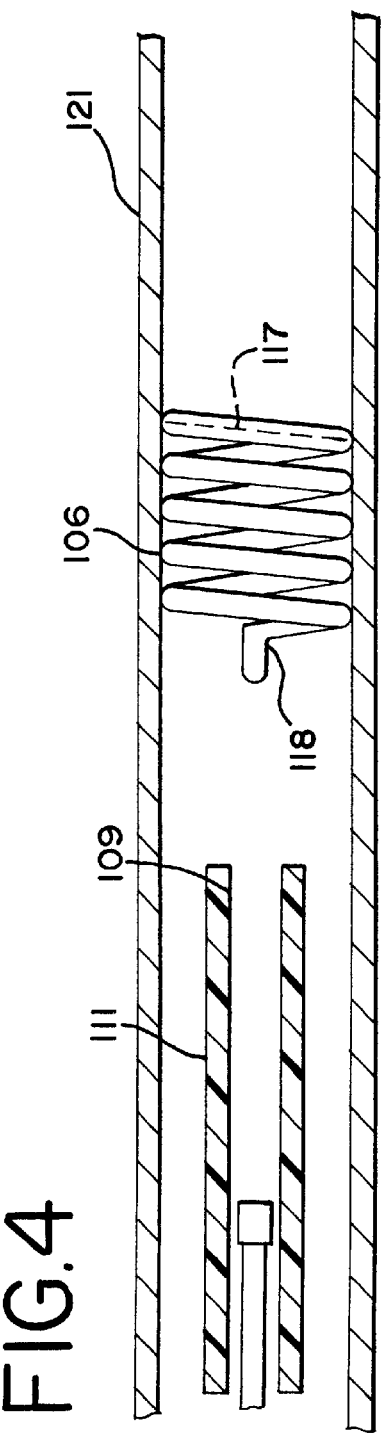

INTRAVASCULAR EMBOLIZATION DEVICE

BACKGROUND OF THE INVENTION

1. Field of the Invention

The present invention relates to a medical device for placing an occlusion device within a vessel and more particularly, relates to a vascular catheter-based embolization system which is used to restrict or block the flow of blood through a vessel.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled, "A Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." Still other examples of embolic coil or stent delivery devices which in these cases incorporate hydraulic fluid delivery systems, are disclosed in co-pending U.S. patent application Ser. Nos. 09/177,848, entitled "Embolic Coil Hydraulic Deployment System," filed on Oct. 22, 1998 and U.S. patent application Ser. No. 09/382,967, entitled "Hydraulic Stent Deployment System," filed on Aug. 25, 1999, assigned to the same assignee as the subject patent application, and are hereby incorporated by reference. All of these patents disclose devices for delivering an embolic device or stent to a preselected position within a vessel of the human body in order to either occlude a blood vessel or to reinforce the walls of a vessel.

In order to occlude a blood vessel by using embolic coils there is usually the requirement that many coils be placed in a single location, and the coils must remain in the position where placed so that thrombus from the blood may form on the coils in order to seal, or partially seal, the space between turns of the coils and the space between coils.

Also, stents have been placed in vessels to prevent restenosis of vessels, or alternatively, to anchor or support fabric mounted on the periphery of the stent to reinforce the walls of a blood vessel.

Such stents which may take the form of a helically wound wire, or tubular-like structures with numerous patterns defining the walls of the device. Examples of various stent configurations are disclosed in U.S. Pat. No. 4,512,338, entitled, "Process For Restoring Patentcy To Body Vessels"; U.S. Pat. No. 5,551,954, entitled, "Biodegradable Drug Delivery Vascular Stent"; and U.S. Pat. No. 4,994,071, entitled, "Bifurcating Stent Apparatus And Method." Stents are generally formed of materials that can retain their shape under the pulsatile flow conditions encountered when placed within the body vessel. Some materials that have been used to make stents include metals and alloys, such as, stainless steel, tantalum, a tungsten and nitinol, as well as polymers such as polyvinyl alcohol (PVA), polyglycolic acid (PGA) and collagen.

Numerous procedures have been developed to enable accurate positioning of stents within a vessel. One such procedure utilizes a helically wound wire loop stent with a relaxed diameter. The stent is wound with a smaller diameter while fixing the ends of the stent. This procedure keeps the stent in a small diameter, tightly wound coil. This system is then delivered by the use of a delivery wire through the lumen of a properly positioned catheter. Once the delivery wire is activated to release the stent, the stent radially expands to its relaxed larger diameter. Such a stent positioning apparatus and method is disclosed in U.S. Pat. No. 5,772,668, entitled, "Apparatus For Placing An Endoprosthesis."

Another stent positioning system utilizes a self-expanding tubular stent. This stent has a relaxed diameter that approximates the diameter of the vessel to be supported. For transport through the catheter, the stent is positioned on a smaller diameter delivery wire. A sheath is positioned over the stent and delivery wire assembly constraining the stent to a smaller diameter. Once the assembly is placed at the desired location in the vasculature, the sheath is withdrawn exposing the stent allowing the stent to return to its predetermined larger size. The expansion of the stent uncouples the stent from the delivery wire while depositing the stent in the vessel at the desired location.

Another stent positioning system utilizes a radially expandable tubular stent formed of a malleable material. This tubular stent has a predetermined expanded diameter defining a lumen that is approximately the same diameter as the vessel to which the stent will be placed. A balloon catheter is placed within the lumen of the stent and the stent is subsequently compressed to a smaller diameter on top of the balloon portion of the catheter. The assembly is then placed within a properly positioned catheter and delivered to the desired location. Inflating the balloon thereby expanding the diameter of the compressed stent deploys the stent. Once the stent is expanded to its predetermined diameter the balloon is deflated and removed leaving the stent deposited at the desired location.

SUMMARY OF THE INVENTION

In accordance with one aspect of the present invention there is provided intravascular embolization device which includes an expandable support element having a relaxed expanded state and a stretched collapsed state, and an embolization element which is mounted on the support element and which serves to substantially prevent the flow of blood through a vessel. More particularly, the support element takes the form of a wire wound in a helical configuration so as to form a plurality of turns when the support element is in its relaxed state and a substantially linear configuration when the support element is in its stretched collapsed state. The embolization element is formed from a flexible elastic material and is attached across one turn of the support element, preferably at the distal end of the support element, so that when the support element is in its relaxed expanded state the embolization element serves to occlude, or partially occlude, a vessel.

In accordance with another aspect of the present invention, the embolization element is formed from a polymer mesh, and preferably from a polyurethane mesh. More particularly, the polyurethane mesh is formed such as to create a plurality of pores each of which have a pore size of about 20 microns.

In accordance with still another aspect of the present invention, the embolization element which is attached to the helically wound expandable support element extends in a plane which is perpendicular to a longitudinal axis of the helically wound support element.

In accordance with still another aspect of the present invention there is provided a vascular occlusive coil deployment system which includes a catheter having a distal section which is formed from a material which exhibits the characteristic that the wall of the distal section of the catheter expands outwardly when fluid pressure is applied within the lumen of the catheter. A deployment system also includes a syringe which is coupled to the proximal section of the catheter for applying a fluid pressure to the lumen of the catheter. In addition, a deployment system includes an intravascular embolization device which includes an expandable support element having a relaxed expanded state and a stretched collapsed state, and an embolization element which is mounted on the support element and which serves to substantially prevent the flow of blood through a vessel. More particularly, the support element takes the form of a wire wound in a helical configuration so as to form a plurality of turns when the support element is in its relaxed state and a substantially linear configuration when the support element is in its stretched collapsed state. The embolization element is formed from a flexible elastic material and is attached across one turn of the support element, preferably at the distal end of the support element, so that when the support element is in its relaxed expanded state the embolization element serves to occlude, or partially occlude, a vessel.

BRIEF DESCRIPTION OF THE DRAWINGS

FIG. 3 is a partial section view of the distal end of the vascular occlusive deployment system with the embolization device expanded in a blood vessel; and, FIG. 4 is a partial section view of the embolization device released from the deployment system and placed within a blood vessel.

DESCRIPTION OF A PREFERRED EMBODIMENT

Figure 1:
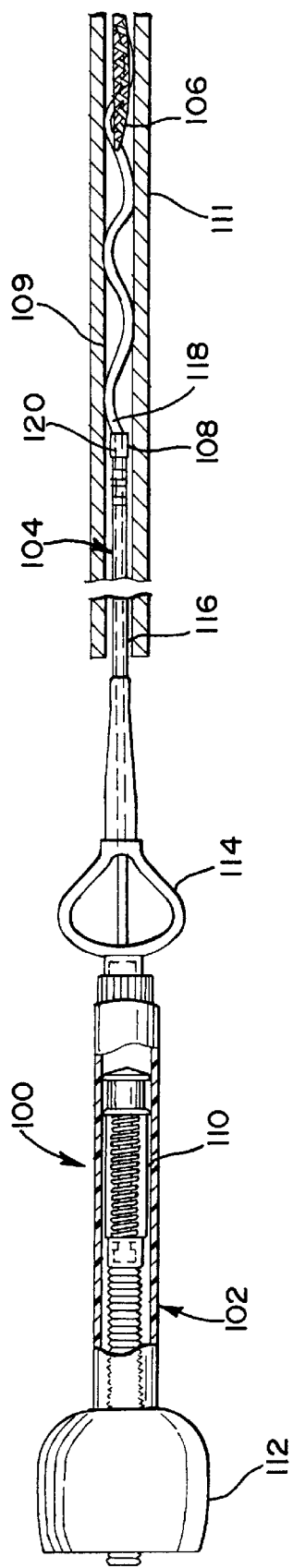
FIG. 1 is a partial section view of the vascular occlusive deployment system with the intravascular embolization device collapsed and disposed within a microcatheter.

FIG. 1 generally illustrates the vascular occlusive deployment system 100 which is comprised of a catheter 104 having a proximal section 116 and a distal section 108, and a syringe 102 is coupled to the proximal section 116 of the catheter 104. The proximal end 118 of an intravascular embolization device 106 is retained by the distal section 108 of the catheter 104. The distal section 108 of the catheter 104 and the intravascular embolization device 106 are slidably disposed within the inner lumen 109 of a microcatheter 111 and is shown in its collapsed state.

As illustrated, the syringe 102 includes a threaded piston 110 which is controlled by a handle 112 for infusing fluid into the interior lumen of the catheter 104. Also, the catheter 104 includes a winged hub 114 which aids in the insertion of the catheter into the vasculature of the body.

The proximal end 118 of the intravascular embolization device 106 is tightly held within the lumen 120 of the distal section 108 of the catheter 104 prior to the release of the embolization device. As the catheter 104 is advanced into a blood vessel, the intravascular embolization device 106 is pushed through a microcatheter 111. The microcatheter 111 is used to assist in navigating the intravascular embolization device 106 through the blood vessels of the body to a site where the embolization device is to be deployed. As may be appreciated, FIG. 1 illustrates the vascular occlusive coil deployment system prior to activation of the piston of the syringe to release of the embolization device.

Figure 2:
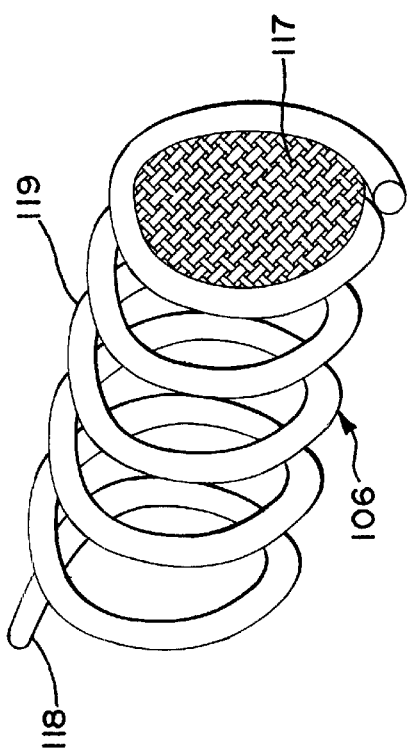
FIG. 2 is an oblique view of the intravascular embolization device in its expanded form.

FIG. 2 illustrates the intravascular embolization device 106 prior to its being collapsed and inserted into the microcatheter 111. The intravascular embolization device 106 includes an embolization element 117 and a support element 119. The embolization element 117 is formed from a flexible elastic mesh or membrane which is substantially impermeable to the flow of blood through the vessel. Preferably the embolization element is formed from braided polyurethane to form a mesh and preferably the pore size of the opening in the mesh is on the order of 20 microns. However, as may be appreciated, the embolization element 117 may be fabricated from many biocompatible materials which exhibit the characteristics of being very flexible and either impermeable or substantially impermeable to the flow of blood.

The support element 119 is formed from a flexible wire which is wound in the form of a helix. The embolization device 106 is delivered through a microcatheter and the support element 119 of the embolization device 106, upon exiting the microcatheter, takes a helical shape to support the embolization element 117, which in turn, restricts or blocks blood flow through the vessel. In other words, as the microcatheter is withdrawn, the support element 119 deploys into its relaxed helical shape and anchors to the wall of the vessel 121. To ensure accurate placement of the intravascular embolization device 106 it is attached to the distal section 108 of the catheter 104 to be released at a desired location. The detachment mechanism may take the form of a hydraulic, electrolytic, thermo-adhesive, or mechanical detachment system. Depending upon the type of detachment system, the proximal end 118 of the intravascular embolization device 106 may be configured to couple to the system.

The support element 119 is preferably formed of a superelastic material, such as a nickel-titanium alloy, in either a wire or tubular form that will return from a collapsed configuration to a helical form. A platinum coil, not shown, may be placed over the proximal end 118 of the support element 119 to provide radiopacity and aid in the delivery of the intravascular embolization device 106.

FIGS. 3 and 4 generally illustrate the release mechanism in action for the vascular occlusive deployment system 100 which is shown in an expanded or released configuration within a blood vessel 121. More particularly, as shown in FIG. 3, the embolization device 106 is shown after being pushed out of the end of the microcatheter 111. When the previously collapsed support element 119 exits the distal section of the microcatheter 111, the pre-formed support element 119 expands from its collapsed state as shown in FIG. 1 to its expanded helical shape as shown in FIG. 3.

As shown in FIG. 4, when a hydraulic pressure is applied to the interior of the catheter 104 the distal section 108 of the catheter 104, which is formed from a low durometer polymer, begins to expand outwardly. As the distal section 108 continues to expand there comes a point in which the proximal end 118 of the support element 119 becomes disengaged from the lumen of the distal section 108 and the intravascular embolization device 106 is then released within the vessel. The catheter 104 may then be withdrawn leaving the coil positioned at the desired site.

In the preferred embodiment, a hydraulic deployment system such as that disclosed in the aforementioned U.S. patent applications Ser. Nos. 09/177,848 and 09/382,967 is utilized to place the intravascular embolization device 106. The proximal section 116 and the distal section 108 of the catheter 104 are formed of materials having different durometers. There are numerous materials which could be used to fabricate the proximal section 116 and distal section 108 of the catheter 104, however, preferably the proximal section 116 is formed from Vestimid material having a durometer in a range of about 62D to 75D. This durometer allows the proximal section to be sufficiently flexible to transverse the vasculature of the human body, but sufficiently rigid to resist any outward expansion of the walls when a fluid pressure of approximately 250 psi is applied to the interior of the catheter.

The distal section 108 of the catheter is preferably formed from a polymer material with a relatively low durometer. The low durometer polymer materials exhibits the characteristic of expanding when a fluid pressure is applied to the interior of the catheter. In the preferred embodiment, when a fluid pressure of between about 150 psi and 565 psi is applied to the interior of the proximal section of the catheter, the walls of the distal section 108 expand outwardly and thereby release the proximal end 118 of the support element 119. In this embodiment, the distal section 108 is preferably formed from a block copolymer, such as Pebax material, having a durometer of between 25D and 55D, with a durometer of 40D being preferred.

With the vascular occlusive deployment system of the present invention, it is possible to place an embolic device very precisely at a desired location within a vessel. Once the device has been positioned at a desired location by use of the catheter, the embolization device may be deployed by applying a fluid pressure to the interior of the catheter to thereby cause the catheter to release the device and deposit the device very accurately at the desired location with the embolization device of the present invention, there is generally no requirement to place numerous devices within a vessel to occlude the vessel since the present embolization device will usually provide sufficient occlusion without the use of additional devices.

As is apparent, there are numerous modifications of the preferred embodiment described above that will be readily apparent to one skilled in the art. These include variations and modifications of the support element 119, including numerous coil configurations. Also, there are obviously variations of the embolization element 117 and of the materials used to fabricate this element. These modifications would be apparent to those having ordinary skill in the art to which this invention relates and are intended to be within the scope of the claims which follow.

That which is claimed is:

1. An intravascular embolization device comprising:
    an expandable support element having a relaxed expanded state and a stretched collapsed state, said support element takes the form of a wire wound in a helical configuration so as to form a plurality of turns in its relaxed expanded state and a substantially linear configuration in its stretched collapsed state, said support element having a proximal end and a distal end; and,
    an embolization element formed from a flexible elastic material which is substantially impervious to the flow of blood and having a substantially circular shape, said elastic material being attached across one turn of the support element at the distal end of the support element to thereby form an embolization device which when placed in a vessel in its relaxed expanded state substantially prevents the flow of blood through the vessel.

2. An intravascular embolization device as defined in claim 1, wherein the embolization element is formed from a polymer mesh.

3. An intravascular embolization device as defined in claim 2, wherein the embolization element is formed of a polyurethane mesh.

4. An intravascular embolization device as defined in claim 3, wherein the polyurethane mesh forms a plurality of pores having a pore size of about 20 microns.

5. An intravascular embolization device as defined in claim 1, wherein the expandable support element is formed from a nitinol-titanium wire.

6. An intravascular embolization device as defined in claim 1, wherein said embolization element extends in a plane which is perpendicular to a longitudinal axis of the expandable support element where the expandable support element is in its relaxed state.

7. An intravascular embolization device as defined in claim 6, wherein the embolization element is formed from a polymer mesh.

8. An intravascular embolization device as defined in claim 7, wherein the embolization element is formed of a polyurethane mesh.

9. An intravascular embolization device as defined in claim 8, wherein the polyurethane mesh forms a plurality of pores having a pore size of about 20 microns.

10. A vascular occlusive coil deployment system comprising:
    a catheter having a tubular wall and having a lumen extending throughout the length of the catheter, said catheter further having a proximal section and a distal section; said distal section of the catheter being formed from a material which exhibits the characteristic that the tubular wall of the distal section of the catheter expands outwardly when fluid pressure is applied within the lumen of the catheter;
    a syringe coupled to said proximal section of the catheter for applying a fluid pressure to the lumen of the catheter; and,
    an intravascular embolization device comprising an expandable support element formed from a flexible wire, said wire being preformed into a plurality of turns to form a helical shape in its relaxed state and a substantially linear shape in its stretched state, said flexible wire having a proximal end which is releasably disposed in fluid-tight engagement with said lumen of the distal section of the catheter; said intravascular embolization device also including an embolization element formed from a flexible elastic material which is substantially impervious to the flow of blood and having a substantially circular shape, said flexible elastic material being attached across one turn of the support element to thereby form an embolization device which when placed in a vessel in its relaxed state substantially prevents the flow of blood through the vessel.

11. An intravascular embolization device as defined in claim 10, wherein the embolization element is formed from a polymer mesh.

12. An intravascular embolization device as defined in claim 11, wherein the embolization element is formed of a polyurethane mesh.

13. An intravascular embolization device as defined in claim 12, wherein the polyurethane mesh forms a plurality of pores having a pore size of about 20 microns.

14. An intravascular embolization device comprising:
    an expandable support element having a relaxed expanded state and a stretched collapsed state, said support element takes the form of a wire wound in a helical configuration so as to form a plurality of turns in its relaxed expanded state and a substantially linear configuration in its stretched collapsed state, said support element having a proximal end and a distal end; and, an embolization element formed from a flexible elastic material which is substantially impervious to the flow of blood and having a substantially circular shape, said elastic material being attached across one turn of the support element to thereby form an embolization device which when placed in a vessel in its relaxed expanded state substantially prevents the flow of blood through the vessel.

15. An intravascular embolization device as defined in claim 14, wherein the embolization element is formed from a polymer mesh.

16. An intravascular embolization device as defined in claim 15, wherein the embolization element is formed of a polyurethane mesh.

17. An intravascular embolization device as defined in claim 16, wherein the polyurethane mesh forms a plurality of pores having a pore size of about 20 microns.

18. An intravascular embolization device as defined in claim 14, wherein the expandable support element is formed from a nitinol-titanium wire.

19. An intravascular embolization device as defined in claim 14, wherein said embolization element extends in a plane which is perpendicular to a longitudinal axis of the expandable support element where the expandable support element is in its relaxed state.

20. An intravascular embolization device as defined in claim 19, wherein the embolization element is formed from a polymer mesh.

21. An intravascular embolization device as defined in claim 20, wherein the embolization element is formed of a polyurethane mesh.

22. An intravascular embolization device as defined in claim 21, wherein the polyurethane mesh forms a plurality of pores having a pore size of about 20 microns.

* * * * *